(12) United States Patent
Vines et al.

(10) Patent No.: US 7,069,170 B2
(45) Date of Patent: *Jun. 27, 2006

(54) WIRELESS VACUUM EXTRACTION MONITORING

(76) Inventors: Victor L. Vines, 7242 Brookcove, Dallas, TX (US) 75214; Robert M. Kennard, 7045 Hillgreen Dr., Dallas, TX (US) 75214; Vince L. George, 6848 Velasco, Dallas, TX (US) 75214; Neil C. VanHooydonk, 2310 Aspen St., Richardson, TX (US) 75082; Darrell L. Vines, P.O. Box 6015, Lubbock, TX (US) 79493

(*) Notice: Subject to any disclaimer, the term of this patent is extended or adjusted under 35 U.S.C. 154(b) by 0 days.

This patent is subject to a terminal disclaimer.

(21) Appl. No.: 10/794,740

(22) Filed: Mar. 6, 2004

(65) Prior Publication Data

US 2004/0199356 A1   Oct. 7, 2004

Related U.S. Application Data

(63) Continuation-in-part of application No. 09/727,006, filed on Nov. 30, 2000, now Pat. No. 6,901,345.

(51) Int. Cl.
*G06L 15/00* (2006.01)
(52) U.S. Cl. .................. 702/138; 606/123
(58) Field of Classification Search ........... 702/138; 606/123; 600/509
See application file for complete search history.

(56) References Cited

U.S. PATENT DOCUMENTS

| 2,831,478 A | 4/1958 | Thoren et al. |
| 3,062,215 A | 11/1962 | Heyns |
| 3,112,749 A | 12/1963 | Sokol |
| 4,014,344 A | 3/1977 | Gutierrez |
| 5,277,557 A | 1/1994 | Cooper |
| 5,298,021 A | 3/1994 | Sherer |
| 5,308,321 A | 5/1994 | Castro |
| 5,395,379 A | 3/1995 | Deutchman et al. |
| 5,569,265 A | 10/1996 | Elliott |

(Continued)

FOREIGN PATENT DOCUMENTS

| BE | 755 528 A | 2/1971 |
| DE | 11 14 278 B | 9/1961 |
| DE | 23 47 850 A | 4/1975 |
| DE | 871 1729 U | 11/1987 |
| GB | 0 839 327 A | 6/1960 |

(Continued)

OTHER PUBLICATIONS www.mityvac.com, 2002.

(Continued)

*Primary Examiner*—Michael Nghiem
*Assistant Examiner*—Xiuqin Sun
(74) *Attorney, Agent, or Firm*—Thrasher Associates (57) ABSTRACT

The invention aids a person who is assisting with fetal extraction by monitoring and recording the pressure inside a vacuum device, and then passing this information wirelessly to a recording and/or displaying device.

12 Claims, 5 Drawing Sheets

U.S. PATENT DOCUMENTS

| | | | |
|---|---|---|---|
| 5,649,934 A | 7/1997 | Smeltzer et al. | |
| 5,982,274 A | 11/1999 | Stelter et al. | |
| 6,074,399 A | 6/2000 | Wallace et al. | |
| 6,289,737 B1 | 9/2001 | Kouketsu et al. | |
| 6,299,691 B1 | 10/2001 | Oda et al. | |
| 6,355,047 B1 | 3/2002 | Wallace et al. | |
| 6,361,542 B1 | 3/2002 | Dimitriu et al. | |
| 6,577,893 B1 * | 6/2003 | Besson et al. | 600/509 |
| 6,620,171 B1 * | 9/2003 | Vines | 606/123 |

FOREIGN PATENT DOCUMENTS

| | | | |
|---|---|---|---|
| JP | 405215633 A | 8/1993 | |
| WO | WO 00 32115 A | 6/2000 | |
| WO | WO 00 32123 A | 6/2000 | |

OTHER PUBLICATIONS www.prismenterprise.com, 2002.

http://www.prismenterprise.com/mityvacob/mityvac.html, 2002.

Bestegen et al: Force and Pressure Measurement During Vacuum Extractions in Obstectrics, 2002.

Reports in Applied Measurement, Hottinger Baldwin Messtechnik, Darmstadt, DE, vol. 9 No. 1, 1995, pp. 1-4.

* cited by examiner

WIRELESS VACUUM EXTRACTION MONITORING

RELATED APPLICATIONS

The present invention is a continuation in part of and claims priority from co-owned U.S. patent application Ser. No. 09/727,006, now U.S. Pat. No. 6,901,345 entitled Vacuum Extraction Monitor with Attachment For Electric Pump by Dr. Victor Vines, filed on Nov. 30, 2000.

TECHNICAL FIELD

The invention relates to childbirth, and more specifically, the invention relates to vacuum extraction deliveries. More particularly still, the invention relates to systems, devices, and methods for monitoring vacuum extraction deliveries.

STATEMENT OF A PROBLEM ADDRESSED BY THIS INVENTION

Interpretation Considerations

This section describes the technical field in more detail, and discusses problems encountered in the technical field. This section does not describe prior art as defined for purposes of anticipation or obviousness under 35 U.S.C. section 102 or 35 U.S.C. section 103. Thus, nothing stated in the Statement of a Problem Addressed by This Invention is to be construed as prior art.

Problem Statement

Complications involved with using vacuum devices include attention being diverted away from the delivery process itself when attention is given to the vacuum pressure being applied to the fetal head. Furthermore, large amounts of activity by different personnel who participate in the delivery may create confusion and chaos in which the monitoring of a vacuum pressure in the vacuum device goes undocumented or worse. The present invention provides a solution that overcomes disadvantages associated with the confusion and chaos existing in the prior art.

BRIEF DESCRIPTION OF THE DRAWINGS

Various aspects of the invention, as well as at least one embodiment, are better understood by reference to the following EXEMPLARY EMBODIMENT OF A BEST MODE. To better understand the invention, the EXEMPLARY EMBODIMENT OF A BEST MODE should be read in conjunction with the drawings in which.

AN EXEMPLARY EMBODIMENT OF A BEST MODE

Interpretation Considerations

When reading this section (An Exemplary Embodiment of a Best Mode, which describes an exemplary embodiment of the best mode of the invention, hereinafter "exemplary embodiment"), one should keep in mind several points. First, the following exemplary embodiment is what the inventor believes to be the best mode for practicing the invention at the time this patent was filed. Thus, since one of ordinary skill in the art may recognize from the following exemplary embodiment that substantially equivalent structures or substantially equivalent acts may be used to achieve the same results in exactly the same way, or to achieve the same results in a not dissimilar way, the following exemplary embodiment should not be interpreted as limiting the invention to one embodiment.

Likewise, individual aspects (sometimes called species) of the invention are provided as examples, and, accordingly, one of ordinary skill in the art may recognize from a following exemplary structure (or a following exemplary act) that a substantially equivalent structure or substantially equivalent act may be used to either achieve the same results in substantially the same way, or to achieve the same results in a not dissimilar way. In addition, statements that an aspect or element of the invention is obvious to one of ordinary skill in an art is applicable to only that specific art, and no other including the art of the invention, unless otherwise indicated.

Accordingly, the discussion of a species (or a specific item) invokes the genus (the class of items) to which that species belongs as well as related species in that genus. Likewise, the recitation of a genus invokes the species known in the art. Furthermore, it is recognized that as technology develops, a number of additional alternatives to achieve an aspect of the invention may arise. Such advances are hereby incorporated within their respective genus, and should be recognized as being functionally equivalent or structurally equivalent to the aspect shown or described.

Second, the only essential aspects of the invention are identified by the claims. Thus, aspects of the invention, including elements, acts, functions, and relationships (shown or described) should not be interpreted as being essential unless they are explicitly described and identified as being essential. Third, a function or an act should be interpreted as incorporating all modes of doing that function or act, unless otherwise explicitly stated (for example, one recognizes that "tacking" may be done by nailing, stapling, gluing, hot gunning, riveting, etc., and so a use of the word tacking invokes stapling, gluing, etc., and all other modes of that word and similar words, such as "attaching"). Further, the discussion herein incorporates all known and foreseeable embodiments of the below-discussed devices, systems, apparatuses, means, and methods. Although modifications to this application may be required by the patent office, no such modifications are wavers of the doctrine of equivalents, or any other rights to equivalents in the invention.

Fourth, unless explicitly stated otherwise, conjunctive words (such as "or", "and", "including", or "comprising" for example) should be interpreted in the inclusive, not the exclusive, sense. Fifth, the words "means" and "step" are provided to facilitate the reader's understanding of the invention and do not mean "means" or "step" as defined in §112, paragraph 6 of 35 U.S.C., unless used as "means for —functioning—" or "step for —functioning—" in the Claims section.

Discussion of the Figures

Figure 1:
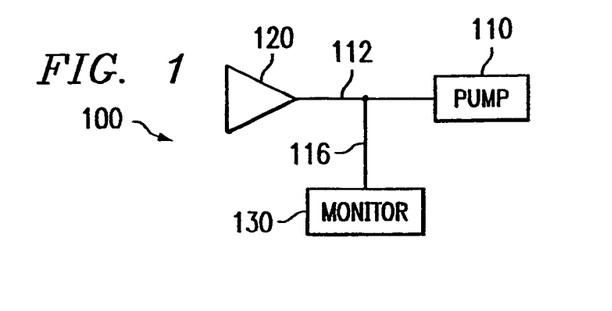
FIG. 1 provides a block diagram of a vacuum device, illustrating systems incorporated by the invention.

Preferably, the invention provides at least the features of monitoring and recording pressures in a suction device used for vacuum-based fetal extraction. Accordingly, FIG. 1 provides a block diagram of a vacuum device 100, illustrating systems incorporated by the invention. A pump 110 which could be a manually activated hand pump, an electric pump, or any other type of air pump, is fluidly coupled to a suction device 120. The suction device 120 is attachable to a fetus, being preferably attachable to fetal head. The suction device 120 is preferably a cup, such as a SILC, a SILASPIC, a SOFT-CUP, or a MALMSTROM-type cup, for example. Fluid coupling between the suction device 120 and the pump 110 may be accomplished by a tube 112, and is preferably a plastic tube.

A recording device 130, which may be a monitor, an enhanced monitor, or a custom-developed device for example, provides a user the ability to monitor air pressures and record air pressures. Accordingly, air pressures may be measured in the monitor 130, or in the tube 112, or in the pump 110. Furthermore, in FIG. 1, a cable 116 couples the tube 112 to the monitor 130. Accordingly, in this embodiment, an air pressure is detected in the tube 112 and converted into information by a device such as a transducer. Next, the detected pressure is passed as information along the cable 116 to the monitor 130.

Figure 2:
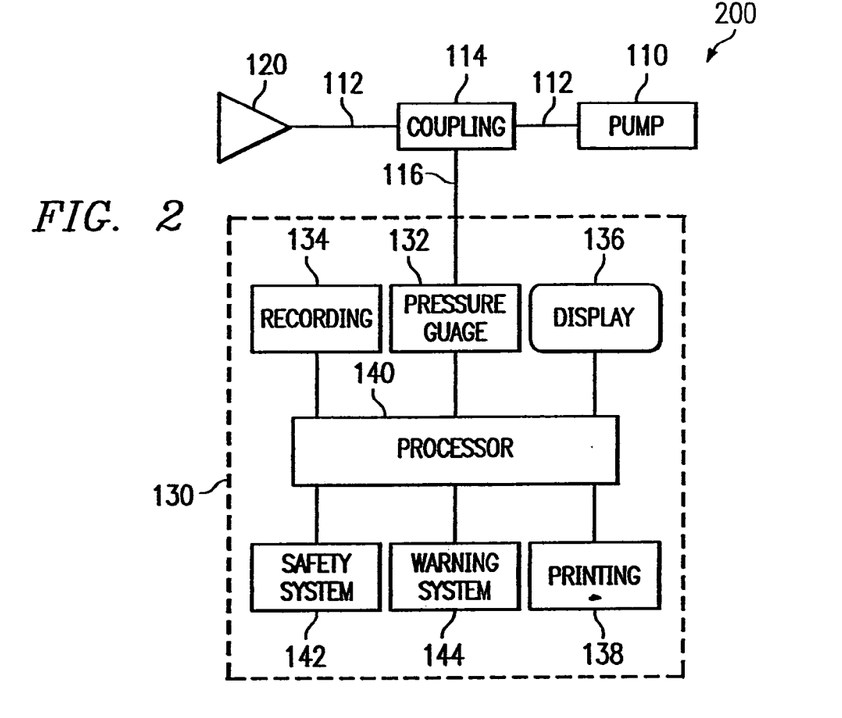
FIG. 2 provides a more detailed block schematic of a vacuum device.

With an initial understanding of the vacuum device 100, one may gain a better understanding of the invention by referring to a more detailed block schematic. Accordingly, FIG. 2 provides a more detailed block schematic of a vacuum device 200. The vacuum device 200 has a pump 110 in fluid communication with the suction device 120 through a tubing 112. The tubing 112, although not illustrated, may contain therein a wire for coupling the pump 110 to the suction device 120 (to provide a device which may support traction tension between the pump 110 and the suction device 120). A coupling 114 is shown dividing the tubing 112. However, it should be understood that the coupling 114 need not be intrusive of the tubing 112, and could be embodied as a cap/tap, for example. In any event, the coupling is enabled to detect the pressure in the tubing (whether the pressure is actually detected in the tubing 112, the suction device 120, or the pump 110). Preferably, the coupling 114 is a plastic tube with a transducer therein. Although not shown in FIG. 2, a transducer in the coupling detects a pressure, and then produces a mechanical or electrical signal based on the pressure detected, or other transportable signal based on the detected pressure (such as a wireless radio frequency communication).

The cable 116 provides a commutative connection between the coupling 114 and a pressure gauge 132 located in the recording device 130. Of course, although the pressure gauge 132 is illustrated as being located in the recording device 130, the pressure gauge 132 could in fact be located in the coupling 114, or along the cable 116. Thus, the pressure gauge 132 functions as a mechanical or electrical signal receiver, which translates a mechanical signal, or electrical signal, or a wireless signal into data that is associated with a pressure.

A processor 140 was coupled to the pressure gauge 132, and provides a means for processing data from the pressure gauge 132 and associating that data with various tables, algorithms, and other information. Furthermore, processor 140 may drive other systems such as a display 136, a printing device 138, warning system 144, or a safety system 142, or send information to a recording device 134. Preferably, the processor is a digital signal processor (DSP), a Pentium processor, or a Strong Arm processor, for example. The processor 140 retrieves various tables, algorithms, and other information from the recording device 134, that preferably stores an electronic record. Preferably, the recording device 134 is embodied as memory, such as RAM, ROM, or removable memory such as Flash RAM, a Memory Stick, or a CD ROM.

The display 136 provides real time information, such as pressures over time, dangerous conditions detected (or other information) to persons assisting with the extraction of the fetus. Preferably, the display 136 is a cathode ray video screen, or a plasma screen.

The printing device 138 provides the ability to print numbers or graphs indicating a pressure over time, progressive pressures detected over time. Preferably, the printing device 138 generates these prints on paper. Furthermore, although illustrated as being integrated into the recording device 130, it should be understood that the printing device 138 may be located externally from the recording device 130.

The safety system 142 causes the implementation of a safety pressure release valve preferably located on the pump 110. When triggered, the safety system 142 may release some of the pressure, or all of the pressure thus returning the pressure inside the tubing 112 to the local atmospheric pressure (or room pressure). The safety system 142 may be embodied as software algorithm for execution in memory, or as mechanical device.

The warning system 144 is for producing a warning when a predetermined pressure or pressures are detected. Typically, the predetermined pressure will be a vacuum pressure, which is lower than a predetermined vacuum pressure, such as 0.2 kgms/cm$^2$–0.8 kgms/cm$^2$, depending on the stage of delivery. The warning may be embodied as a light, a sound, or a voice, for example. A light may flash at different rates, or present different colors, or present different intensities as pressure changes in the tube. Similarly, a sound may change in tone as different pressures are detected, or a voice may verbally indicate a pressure or a warning condition. Furthermore, the warning system may be used to trigger and provide information to the safety system 142.

Figure 3:
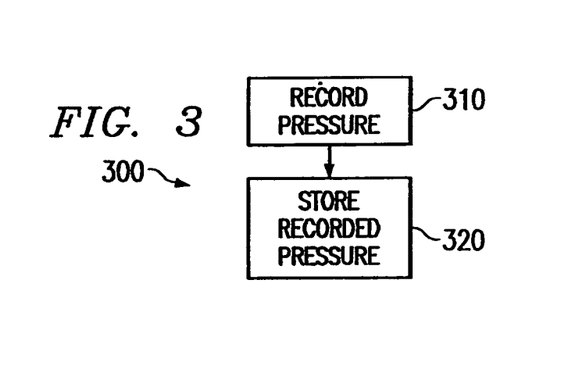
FIG. 3 provides a flowchart of a recording algorithm that illustrates one embodiment of the invention.

A better understanding of the invention may be achieved by examining the operation of the invention. FIG. 3 provides a flowchart of a recording algorithm 300. First, in a record pressure act 310, the recording algorithm 300 records a pressure, which exists in a vacuum device. Then, in a store recorded pressure act 320, the recording algorithm 300 creates a permanent record of the pressure which was recorded in the record pressure act 310.

Figure 4:
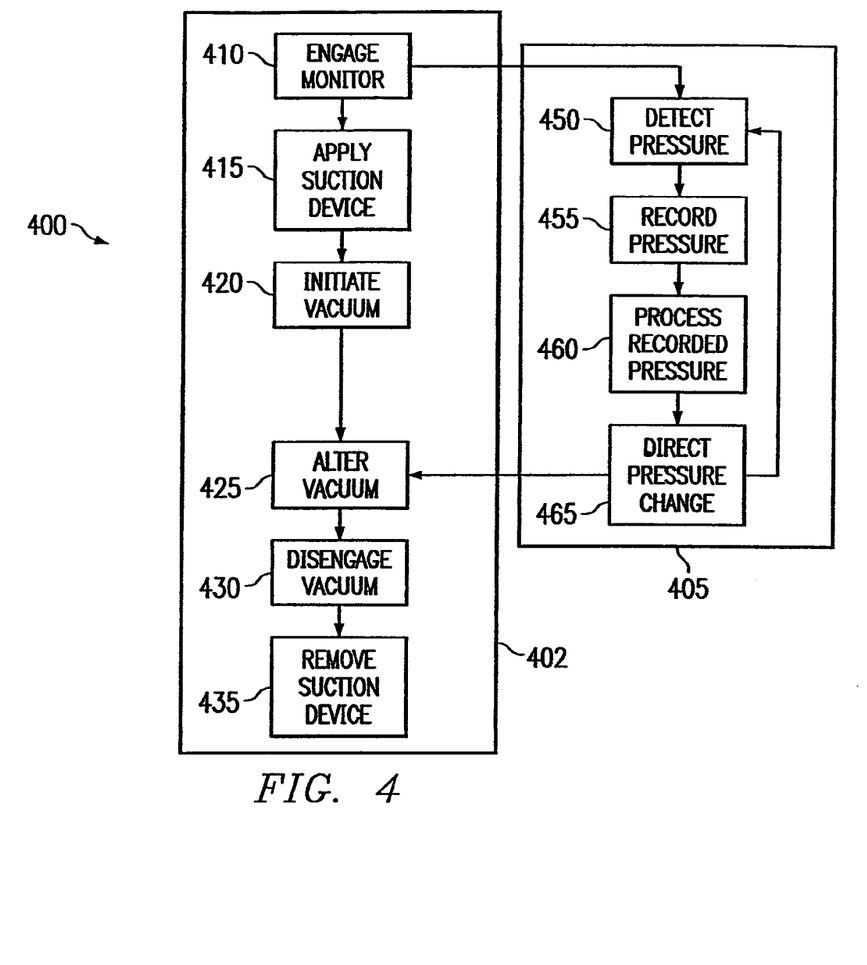
FIG. 4 illustrates a block flow diagram of a vacuum device algorithm that implements one embodiment of the invention.

An even better understanding of the invention may be realized by examining the processes flow of a vacuum device embodied according to the invention. Accordingly, FIG. 4 illustrates a block flow diagram of a vacuum device algorithm 400 that implements one embodiment of the invention. The vacuum device algorithm 400 comprises a pump algorithm 402 for illustrating acts performed with a vacuum device pump, and a monitor algorithm 405 illustrating acts associated with a recording device. The vacuum device algorithm 400 begins in a pump algorithm 402.

The pump algorithm 402 is initiated in an engage monitor act 410. The engage monitor act may include attaching a cable between a vacuum pump and a recording device, and then turning on the recording device. After the engage monitor act 410, the pump algorithm 402 proceeds to an apply suction device act 415 in which a suction device is attached to a fetus, and preferably a fetal head. It should be noted that in the apply suction device act 415, if a disposable MITYVAC is being used in the procedure, adapters should be attached to suction tubing of the vacuum device and the disposable MITYVAC assembly. Prior to applying the suction device to the fetus, the apply suction device act 415 calibrates, or zeros, the monitor so that the pressure detected prior to applying a vacuum to the fetus is recognized as being the local atmospheric pressure. Likewise, prior to the application of a vacuum to a fetus, the monitor is initialized, or "zeroed," to local atmospheric conditions.

Following the apply suction device act 415, the pump algorithm 402 proceeds to an initiate vacuum act 420. In the initiate vacuum act 420 a vacuum pressure is created in the vacuum device by manually actuating a manual pump, or by engaging the vacuum switch or trigger in an electric pump. The next act in the pump algorithm 402 changes the vacuum pressure. This is accomplished in an alter vacuum pressure act 425, and is typically employed as a result of a response received from the monitor algorithm 405. Of course, altering the vacuum pressure may not be necessary during a vacuum extraction procedure, and thus the alter vacuum pressure act 425 should especially be viewed as an optional act for the present embodiment (although the only needed acts are explicitly articulated in the claims).

Next, a disengage vacuum act 430 is performed when the pressure in the vacuum device is returned to at least local atmospheric pressure. Furthermore, the pressure may be raised to a pressure greater than local atmospheric pressure to encourage the suction device to separate from the fetus. Then, the vacuum device algorithm 400 and pump algorithm 402 end together in a remove suction device act 435, in which the suction device is removed from the fetus. Furthermore, in the remove suction device act 435 the recording device may be disengaged, and the record of the pressures detected during the vacuum device algorithm 400 may be stored in a permanent medical record, which may be a physical paper record and/or an electronic record.

The monitor algorithm 405 initiates in a detect pressure act 450, which begins in response to the initialization of the recording device in the engage monitor act 410. In the detect pressure act 450 a pressure in the vacuum device is detected, which will typically be between a room (or atmospheric) pressure and vacuum pressure (meaning a pressure lower than the local atmospheric pressures). Next, the vacuum device algorithm 400 continues to a record pressure act 455. In the record pressure act 455 the pressure detected in the detect pressure act 450 is automatically recorded (or stored), preferably by an electronic means (such as a memory) or by a paper means. Furthermore, the record pressure act 455 may include the displaying of the recorded pressure on a monitor or other display.

The recorded pressures are monitored and processed in a process recorded pressure act 460. The process recorded pressure act 460 evaluates the detected pressure in a warning system, and may direct the displaying or printing of additional information in response to the warning system. [The process-recorded pressure 460 may include a sub-act of displaying the processed information on the display device, such as a monitor.] Likewise, if the process is recorded at 460 determines if the detected pressure exceeds a predetermined pressure, the process recorded pressure act 460 may direct a pressure change, such as a lower pressure, or an immediate return to local atmospheric pressure, in a direct pressure change act 465. The direct pressure change act 465 produces the electrical or mechanical signals needed to implement the alter-vacuum pressure act 425.

The invention provides the ability to accurately measure, record, and trace pressure events that transpire in a vacuum device during vacuum extraction. Accordingly, the invention assist physicians, hospitals, and other delivery personnel in the defense of accusation that proper guidelines were not followed during the vacuum extraction. Furthermore, those who suffer from improper vacuum extraction also have access to a permanent medical record, which should facilitate mediated settlements, and avoid the costs of lengthy discovery and emotionally scaring litigation. Also, because data will be collected with each vacuum extraction, the guidelines for the conduct of a vacuum extraction may be changed and improved to more accurately be able to predict safe guidelines for a vacuum extraction delivery.

Figure 5:
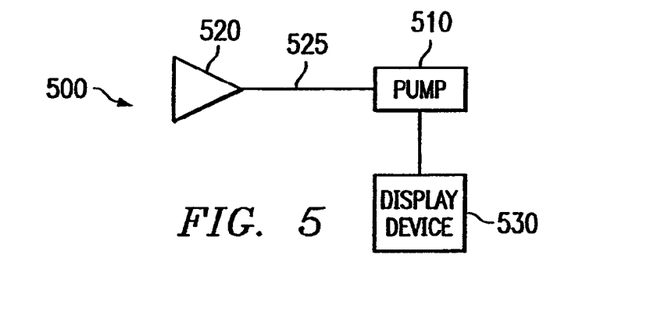
FIG. 5 provides a block diagram of an adapter assembly that provides existing vacuum devices the features of the invention, and is accordingly another embodiment of the invention.

It will sometimes be advantageous to provide existing vacuum devices the ability to access the advantages provided by the invention. FIG. 5 provides a block diagram of an adapter assembly 500, which provides existing vacuum devices access to advantages of the invention, and is accordingly another embodiment of the invention. The adapter assembly 500 comprises a pump 510 fluidly coupled to a suction device 520 by a tubing 525. A display device 530 is connected to the pump 510. Preferably, the display device 530 is coupled to the pump 510 via an adapter to the pump 510. Better understanding of the adapter assembly 500 may be achieved by examining specific embodiment.

Figure 6:
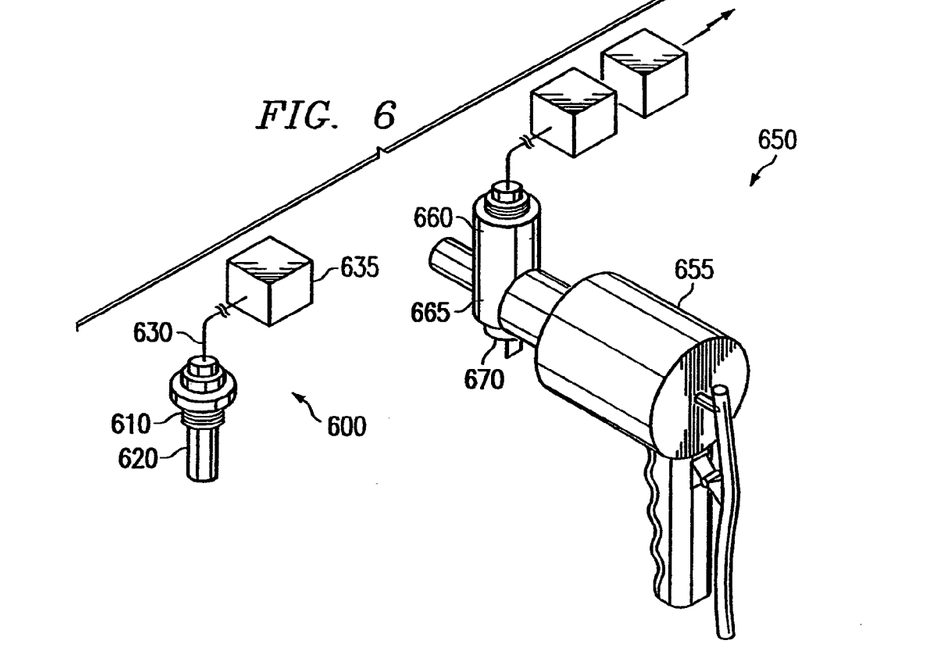
FIG. 6 illustrates a pump attachable device capable of attachment to an electrical pump.

FIG. 6 illustrates a pump attachable device 600 capable of attachment to an electrical pump 655. The pump attachable device 600 has an adapter 610, such as the threaded fittings illustrated in FIG. 6. Furthermore, the pump attachable device 600 has a pressure transducer 620, which detects a pressure and converts the detected pressure to a mechanical or electrical signal capable of being transferred to a monitor (not shown) via a cable 630. The cable 630 includes a plug 635 capable of attachment to a monitor or other recording device.

Also, illustrated in FIG. 6 is a pump system 650 having a pump attachable device attached thereto. The pump system 650 includes an electric pump 655 such as a MITYVAC, or disposable MITYVAC, for example. The electric pump 655 has a front end 665, which has a cavity for supporting other devices and for transporting the pressures, including the vacuum pressure, created by the electric pump 655.

The front end 665 has thereon a pressure gauge receiver 660. Typically, the pressure gauge receiver 660 accepts a pressure gauge that mechanically detects a pressure, which is then displayed for those performing the vacuum procedures. In operation of one embodiment of the invention, the pressure gauge is removed from the electric pump, typically by unscrewing the pressure gauge, and the pump attachable device 600 is then inserted into the pressure gauge receiver 660. Also provided by the front end 665 is a pressure release valve 670. The pressure release valve 670 allows the inflow of air into the front end, and particularly into the cavity of the front end, in order to increase the pressure in the vacuum device.

Figure 7:
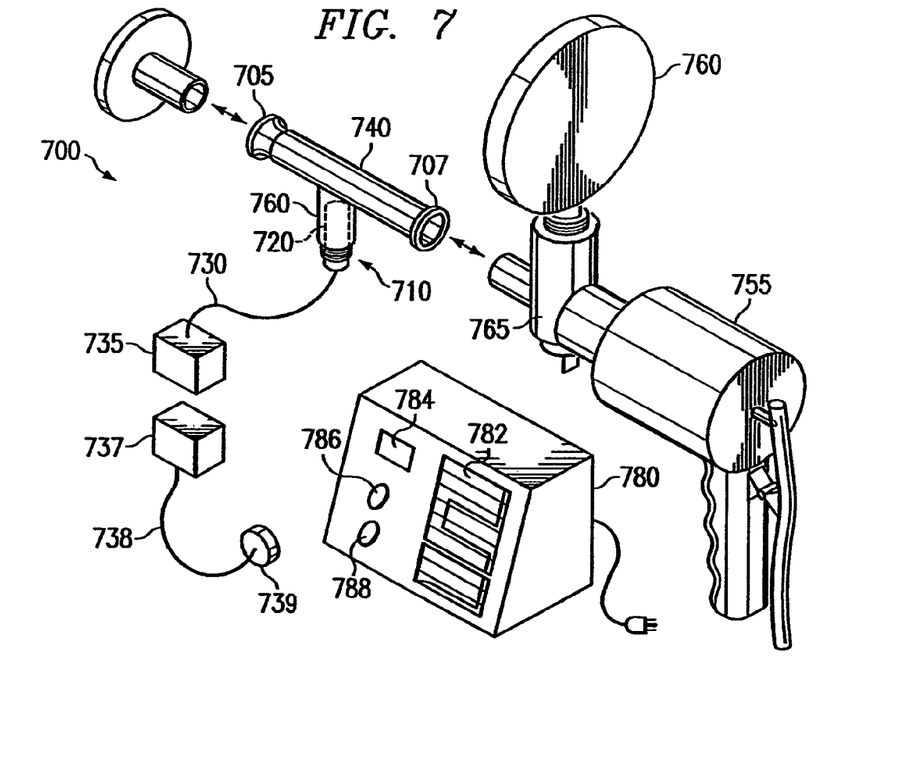
FIG. 7 as a tube attachable device.

Another embodiment of the invention is illustrated in FIG. 7 as a tube attachable device 700. The tube attachable device 700 includes a first end 705, and a second end 707. The first end 705 is preferably configured to either attach to a plastic tube section, or a suction device. The second end 707 is preferably configured to attach to a tube, or a front end such as the front end 765 that is adapted to receive the second end 707. The tube attachable device 700 includes tubing 740, which is preferably plastic tubing.

The tubing 740 includes a pressure gauge receiver 760. Accordingly, a transducer/pressure gauge 720 is inserted into the tubing 740 and secured in the tubing by an adapter 710. Furthermore, pressures detected by the pressure transducer 720 are converted into a data signal that is sent to a recording device along a cable 730. The cable 730 also includes a plug 735, which is connectable to the recording device monitor 780, or to a second plug 737. The plug 737 couples an extension cord 738 to a second plug 739. The second plug 739 is also attachable to the recording device 780 at a plug socket 788.

The vacuum device illustrated in FIG. 7 includes a pump 755, which provides a disposable MITYVAC, and a pressure gauge 760, which is fitted into the front end 765. Thus, the vacuum device provides a physician the advantage of having a mechanical visual display provided by the gauge 760 (thus requiring little change by those who are accustom to viewing the mechanical gate 760), as well as providing mechanical and electric displays and printouts of the recorded pressures while the recording device 780.

The recording device 780 may produce a printed-paper record 782, as well as a visual display 784. Of course, the printed-paper record 782 or the visual display 784 may print or display numbers, graphical representation or other indicia of the pressures being detected in the vacuum device. Furthermore, the recording device 780 provides a warning device 786 which could produce a light, sound, or a vocalized recording of a warning to those assisting with the fetal extraction.

Figure 8:
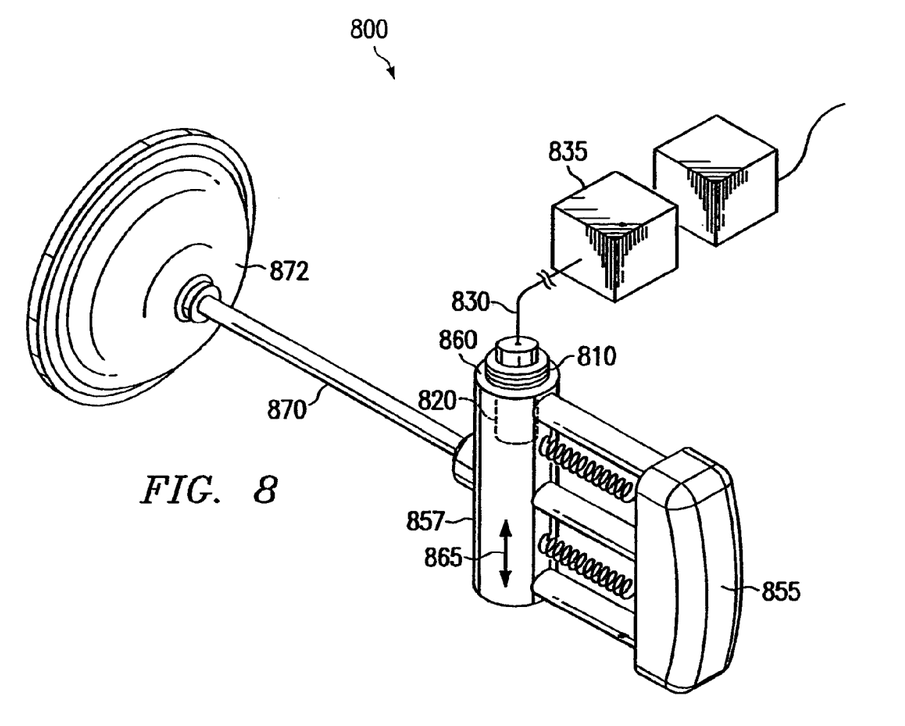
FIG. 8 illustrates a pump attachable device configured to attach to a hand pump, such as a KIWI hand pump.

FIG. 8 illustrates a pump attachable device 800 configured to attach to a hand pump 855, such as a KIWI hand pump. The pump attachable device 800 includes an adapter 810, such as threading, gaskets, or other attachments capable of forming a fluid-tight seal, a pressure-recording device 820, such as a transducer, and a cable 830 for communicating a detected pressure to a recording device via a plug 835. The hand pump 855 includes a handle 857, which maintains a vacuum cavity 865 therein. The vacuum cavity 865 is fluidly connected to a hose 870 and a suction device 872. The handle 857 also includes a pressure gauge receiver 860. In an unmodified hand pump, the pressure gauge receive 860 accepts a mechanical pressure gauge that mechanically indicate a detected pressure in the vacuum cavity 865. In the vacuum device according to the present embodiment of the invention, the pump attachable device 800 is secured into the handle 857 of the hand pump 855 via the pressure gauge 860.

Figure 9:
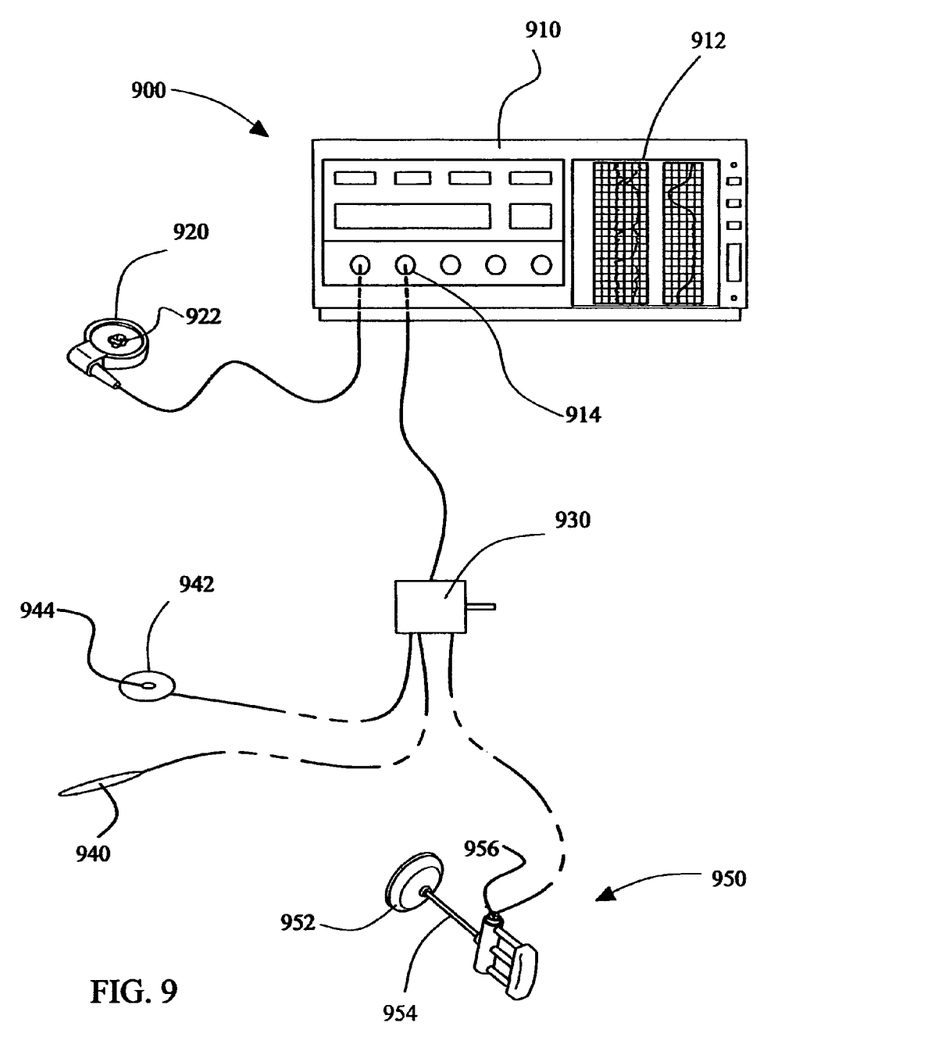
FIG. 9 illustrates a vacuum extraction monitoring system 900 that incorporates a fetal/maternal monitor 910

FIG. 9 illustrates a vacuum extraction monitoring system 900 that incorporates a fetal/maternal monitor 910. Sometimes the fetal/maternal monitor is called in practice or literature by a variety of names, such as a fetal heart rate monitor, a maternal monitor, or a fetal monitor. To simplify discussion below, the monitor known by these and other names is referred to as a fetal monitor 910. One such exemplary monitor is the Series 50 XM Fetal/Maternal Monitor from HEWLETT PACKARD™, however it is appreciated that other monitors from other manufacturers are available and can be incorporated within the invention. The monitoring system 900 generally includes the fetal monitor 910, and maternal heart rate monitor 920, an intrauterine pressure transducer (also known as the intrauterine pressure catheter, or IUPC) 940, an external uterine monitoring device 942, and a vacuum pump 950.

The fetal monitor 910 is a device that is intended for monitoring fetal heart rate, uterine activity, and maternal heart rate. The fetal monitor 910 can also monitor maternal SpO$_2$ and maternal blood pressure non-invasively. Other than these factors, and prior to this invention, the fetal monitor 910 is not known to monitor or record additional delivery factors. Prior to labor, the fetal monitor 910 monitors fetal and maternal heart rates, as well as contractions.

After rupture of the maternal membranes, a fetus's heart rate can be monitored directly by applying a transducer to the fetal scalp, and uterine activity can be monitored by an intrauterine pressure catheter (IUPC) 920. During a delivery operation, both fetal heart rate and maternal uterine activity are displayed on the fetal monitor and recorded on trace paper 912. In addition, maternal parameters are typically shown on the fetal monitors' backlit display, and are also recordable as traces on trace paper. The fetal monitor 910 is discussed further, below.

The heart rate patient transducer 920 is an external monitoring device that is used to detect and display the heat rates of both a patient (mother) and at least one fetus. In a preferred embodiment, the heart rate patient transducer 920 attaches to a patient's abdominal area through the use of a gel 922, as is well known in the art. The heart rate of the both the patient (mother) and the fetus should be monitored during fetal extraction, and thus the heart rate patient transducer 920 is preferably engaged with the fetal monitor 910 during the entire delivery process. However, there are additional methods of detecting the heart rate of a child during fetal extraction such as direct placement of a heart rate fetal transducer on the fetus' head, as is known in the art (this often achieves a more reliable reading). Of course, any known and accepted method of monitoring the heart rate of the patient or the fetus can be used with the invention without departing from the scope of the invention.

The intrauterine pressure catheter (IUPC) 940 detects intrauterine pressure during labor. Accordingly, during labor, the IUPC 940 is inserted between the surface of a uterus and the head of the fetus in the uterus. Then during labor, pressure placed on the IUPC 940 activates a transducer in the IUPC 940 that converts a mechanical indication of the intrauterine pressure into an electrical signal that is in turn processed by the fetal monitor 910.

It is frequently desirable to monitor intrauterine pressure prior to the appearance of the fetus because when the IUPC 940 detects and indicates a high pressure, it may indicate that a push, or contraction of the uterus, is taking place. It is during these contractions that an assisting physician can effectively assist the patient in making the fetus appear. In practice, during vacuum extraction, uterine contractions are measured at least until the fetus head appears, at which point a vacuum extraction cup may be attached to the fetus' head. Prior to the present invention, after the vacuum extraction cup is attached to the fetus head, contractions are not monitored and so the IUPC 940 is removed. However, the present invention preferably incorporates a switch 930 (discussed below), which enables contractions to be monitored throughout the delivery process.

Following the appearance of the head, the IUPC 940 is removed, the vacuum pump 950 is attached, and preferably an external uterine monitoring device (EUMD) 942 is used to monitor uterine contractions. The EUMD 942 is placed externally on the abdominal area of the patient, typically with a small gel application 944, as is known in the art. Upon a contraction by the patient, a transducer in the EUMD 942 stretches and emits a small electrical signal in proportion to the stretch and to the input voltage of an input device (the fetal monitor 910 in this example). The electrical signal is in turn processed by the fetal monitor 910 to indicate that a contraction is taking place. The use of the EUMD 942 allows a physician to monitor contractions while delivering a fetus with a vacuum pump, and thus to synchronize pulls with contractions to facilitate delivery.

The IUPC 940, the EUMD 942, and the vacuum pump 950 are coupled to the fetal monitor 910 via the switch 930. The switch 930 may operate as a single-function selection switch so that an attendant may monitor one of the monitoring devices, or vacuum pump input. For example, the switch may allow one to monitor the IUPC 940, the EUMD 942, the vacuum pump 950, or other devices that are known or may develop in the art. In addition, the switch 930 may place the IUPC 940, the EUMD 942 and the vacuum pump 950 in simultaneous operation (either two devices at a time or all three devices at a time). In single-function mode, only one attached device is monitored and displayed on trace paper, which lowers the likelihood of confusion due to copious signals, and makes the display more clear.

In simultaneous operation, the fetal monitor 910 displays multiple device readings, and may do so by sampling the IUPC channel(s), the EUMD channel(s), and/or the vacuum pump's channels simultaneously or alternatively so that multiple factors may be monitored at the same time. Alternatively, the attached devices may have transducers that are timed to send alternating signals such that the parameters monitored by the devices can be viewed simultaneously. The choice of viewing one parameter, or multiple parameters, should be left to the attending physician based on the physician's personal preference.

Since the electromechanical structure of a switch is well known in the electrical arts, the structure of the preferred switch 930 is not discussed here. However, it is desired that the switch 930 have at least two inputs, and a preferred embodiment of the switch 930 has three inputs. Typically, the input is a female-type electrical plug, but may be male, of course. In addition, the switch has an input for the IUPC 940, an input for the EUMD 942, and an input for the vacuum pump 950. The input for the vacuum pump 950 preferably includes a first line for vacuum pressure data, and a second line for traction force data. Of course, the input for the vacuum pump 950 may monitor only one data line, and the data lines may be split into two input lines—a vacuum pressure input and a traction force input.

Monitoring Vacuum Pressure in Vacuum Extraction Monitoring System

Some confusion may be encountered when speaking of a vacuum pressure. A vacuum pressure is generally understood to mean a pressure lower than the local atmospheric pressure, such that when one says the vacuum increases, in reality the difference between the atmospheric pressure and the pressure of the vacuum is increasing while in purely scientific terms the pressure is in fact decreasing.

Thus, a vacuum contrasts with the most common scientific understanding of air pressure, as measured in, for example, centimeters or millimeters of mercury (the mercury system). In the mercury system, 0 mm mercury is an absolute vacuum (this is theoretically impossible), and 76 cm mercury (29.92 inches of mercury) is widely regarded as the "average" atmospheric pressure at sea level. As one goes below sea level, pressure increases (which can lead to pressure implosion). Similarly, as one goes higher into the atmosphere, pressure decreases, indicated by a lower millimeter of mercury value. Pressure also varies inversely with temperature.

Accordingly, "increasing the vacuum," means that a higher vacuum pressure is reached, but a lower absolute pressure is reached. However, these differences are understood and appreciated by those of ordinary skill in the mechanical arts, including most physicians. Accordingly, the present invention utilizes a pressure transducer in the vacuum pump 950, or located somewhere between the vacuum cup 952 and the fetal monitor 910, which transforms a mechanical vacuum into an electrical signal. The selection of the transducer is more fully discussed below. One advantage of providing a pressure reading in millimeters or centimeters of mercury include the advantage of providing a trace paper read-out as being "positive" information. Interestingly, the preferred measure indication is that of a "positive value", which in fact represents a number of cm Hg below local atmospheric pressure.

Stated another way, physicians are familiar with a fetal monitors' uterine activity channel 914, and its paper tracing which reads from zero (0) to one hundred (100). An "upward" input deflection on the trace paper 912 indicates an increase in intrauterine pressure (the intrauterine pressures are periodically measured and then displayed on the trace paper 912). These displayed pressures are shown in millimeters of mercury. The invention takes advantage of this to provide physicians a display of vacuum device "vacuum pressure."

When monitoring the vacuum pressure with the present invention the vacuum proximate to the vacuum device is measured and displayed and recorded in centimeters of mercury. It is preferred that the output voltage of the transducer is linear with respect to a limited range of supply voltage, and it is also preferred that the output voltage is independent of any frequency in the supply voltage. In addition, the transducer is arranged in the pump so that as a higher vacuum is reached in the vacuum device, it is displayed on the trace paper as an increasing numeric value, ranging from zero on the trace paper corresponding to local atmospheric pressure (roughly 76 cm Hg), to 76, which would actually correspond with −76 cm Hg, which is an absolute vacuum. Note that different values of local atmospheric pressure are possible, depending on the temperature and altitude.

To achieve the correct scaling for display on the graph, the invention uses a transducer 956 that produces four microvolts per centimeter of mercury of pressure per volt provided by the attached fetal monitor. Using this standard, for example, a vacuum of ten centimeters of mercury should cause a voltage of forty microvolts in the transducer for each volt of voltage supply from the fetal monitor (sometimes called the "excitation voltage). The transducer 956 is likewise connected to the Intrauterine Pressure Channel (IUPC) 914 to display vacuum values in centimeters of mercury on the trace paper 912, the display representing cm Hg below relative atmospheric pressure.

Display Example for Monitoring Vacuum Pressure

Physicians appreciate that the scale of trace paper ranges from one (1) to one hundred (100). For intrauterine pressure measurement, this indicates millimeters of mercury, and nearly the entire graph is used. However, for vacuum device utilization, this same trace paper preferably displays centimeters of mercury. Those of skill in the art will appreciate that the range of the vacuum is also large—from zero (local atmospheric pressure) to a very large vacuum value (since a perfect vacuum is roughly seventy-six (−76) centimeters of mercury, which is obviously below the one hundred (100) maximum value printed on the chart). In any event, each cmHg lower than local atmosphere that is detected shows on the trace paper as an increase of one cmHg.

For example, if the pressure inside the vacuum cup 952 is 8 cm Hg, and local atmospheric pressure is 76 cm Hg, the "vacuum pressure" will be represented on the trace paper as 68 cmHg. Similarly, a "vacuum pressure" reading of 33 cm Hg would be displayed as 43 cmHg on the trace paper. Of course, another transducer could be selected to illustrate other measures of pressure to achieve similar effects, such as inches of water. Similarly, if another fetal monitor is used, the sensitivity of the transducer should match the input specification of the equipment manufacturer of the fetal monitor, and specifically, the input specification for the voltage signal (excitation voltage) on the intrauterine portion of the trace paper.

Monitoring Traction Force

Sometimes, one may desire to detect and record traction forces induced on the vacuum pump 950 during fetal delivery. To use existing fetal monitors to detect and record traction forces, a transducer that is capable of correctly producing an electric signal based on the traction force is needed. Thus, to detect and record the traction force, a tether 954 is attached to the vacuum cup 952 and to a transducer within the vacuum pump 950 so that the transducer can convert the tension force in the tether 954 into an electric signal. In a preferred embodiment, a transducer is coupled between the tether and the fetal monitor 910 such that the transducer produces four microvolts of signal per each pound of tension force detected in the tether 954 per each volt of excitation voltage produced by the fatal monitor 910.

Wireless Monitoring

It may be desirable to incorporate wireless features into the devices and systems taught by the invention in order to reduce clutter and confusion in the delivery room, and to facilitate a more automated operation of the invention. Accordingly, in an alternative method of the invention, data is routed wirelessly to a recording device, such as an existing fetal monitor. One method of achieving this process is to use a means for transmitting, such as a transmitter or a transceiver, for example, comprised in a vacuum extraction device, to transmit a wireless signal to a means for receiving, such as a receiver or transceiver, for example, comprised in a monitor.

Methods of wireless communication are well known in the electrical communication arts, and include: amplitude modulation, frequency modulation, or packet-data communications such as IEEE 802.11 series communication protocols, for example. Of course, additional data communication methods will be developed in the electrical communications arts, and all these methods, including foreseeable methods, are incorporated within the scope of the claims. In practice, any data or signal transmission achieved in an aforementioned method may be achieved wirelessly.

Wireless communications means include receivers for receiving wireless communications, transmitters for transmitting wireless communications, and transceivers which are single devices, which a receiver portion and a transmitter portion, and which are capable of both sending and receiving wireless communications. In practice, one may replace a cable or a number of cables in an aforementioned exemplary device with a transmitter/receiver/transceiver combination. Although such combinations are apparent to those of skill in the electrical communications arts, it bears pointing out that, for wireless operation, a vacuum extraction device preferably comprises a transmitter or transceiver, while a monitor (including existing monitors modified as described in the discussion of FIG. 9, for example) or recorder preferably comprises a receiver or transceiver. Thus, in practice a vacuum pressure will be detected in a fetal extraction device as a vacuum pressure reading, the vacuum pressure reading is then wirelessly transmitted to a monitor where the vacuum pressure reading is recorded.

Of course, other features and embodiments of the invention will be apparent to those of ordinary skill in the art. After reading the specification, and the detailed description of the exemplary embodiment, these persons will recognize that similar results can be achieved in not dissimilar ways. Accordingly, the detailed description is provided as an example of the best mode of the invention, and it should be understood that the invention is not limited by the detailed description. Accordingly, the invention should be read as being limited only by the claims.

We claim:

1. A device for recording a pressure produced by a vacuum extraction device, the vacuum extraction device enabled to couple to a fetus via a suction device, comprising:
   a wireless communication system comprising a receiver in a monitor, the monitor being enabled to record a detected pressure;
   a pressure detection device comprising a transmitter, the pressure detection device adapted to couple to a cavity of a vacuum extraction device for use with fetal extraction, such that the pressure detection device is enabled to detect a pressure in the cavity;
   the pressure detection device further adapted to communicate a detected vacuum pressure to the monitor via the transmitter;
   the vacuum extraction device being adapted to produce a vacuum therein via hand-actuation; and
   the vacuum extraction device comprising a suction device being vacuum attachable to a scalp portion of a fetus.

2. The device of claim 1 wherein the receiver is a receiver portion of a transceiver.

3. The device of claim 1 wherein the transmitter is a transmitter portion of a transceiver.

4. A vacuum extraction device for aiding a person who is assisting with fetal extraction, comprising:
   a suction device that is enabled for vacuum attachment to a fetus;
   a pump that is capable of producing a vacuum pressure;
   a tubing that fluidly couples the suction device to the pump;
   a means for detecting a vacuum pressure comprising a transmitter coupled between the vacuum device and the suction device; and
   a means for automatically recording a vacuum pressure comprising a receiver communicatively coupled to the means for detecting a vacuum pressure.

5. The device of claim 4 wherein the receiver is a receiver portion of a transceiver.

6. The device of claim 4 wherein the transmitter is a transmitter portion of a transceiver.

7. A method of aiding a person who is assisting with fetal extraction, comprising:

attaching a suction device to a fetus by placing the vacuum device on the fetus and then inducing a vacuum pressure in the suction device;

detecting the vacuum pressure;

transmitting the detected pressure wirelessly;

receiving the detected pressure wirelessly at a recording device; and automatically recording the vacuum pressure.

8. The device of claim 7 wherein the vacuum device comprises a means for transmitting a wireless signal.

9. The device of claim 7 wherein the monitor comprises a means for receiving a wireless signal.

10. A method of using a recording device to record a pressure in a vacuum extraction device, comprising:

wirelessly coupling a recording device comprising a receiver to a vacuum extraction device comprising a transmitter;

placing the vacuum extraction device on a fetus, the space between the fetus and the vacuum extraction device defining a pressure area in the vacuum extraction device, the vacuum extraction device adapted to couple to a fetus via a suction device;

inducing a vacuum pressure in the pressure area by hand-actuating the vacuum extraction device;

detecting the vacuum pressure in the pressure area to generate a vacuum pressure reading;

wirelessly transmitting the vacuum pressure reading;

wirelessly receiving the vacuum pressure reading; and recording the vacuum pressure reading to produce a record.

11. The method of claim 10 wherein the vacuum device employs a pump to generate a vacuum, the pump being a vacuum extractor, comprising:

a vacuum cup having a cup portion for application to a fetus, the cup portion defining a cup chamber;

a handle connected to the vacuum cup, the handle including a grip surface, the handle for maneuvering the vacuum cup; and a vacuum pump defining a vacuum chamber fluidly couplable to the cup chamber, wherein the vacuum pump includes an activation surface for creating a vacuum in the vacuum chamber, wherein the grip surface of the handle and the activation surface of the vacuum pump are in a proximity such that a single human hand can grasp both the grip surface and the activation surface simultaneously, wherein compression of the activation surface of the vacuum pump towards the grip surface of the handle reduces the volume within the vacuum chamber.

12. A vacuum extraction pump-attachable device that monitors a vacuum pressure in a vacuum extraction device, comprising:

an adaptor enabled to attach to a pressure gauge receiver of a hand actuated vacuum extraction device, the vacuum extraction device comprising a suction device adapted to couple to a scalp portion of a fetus;

a vacuum pressure detector secured in the adapter such that the vacuum pressure detector is exposed to an air cavity in the vacuum extraction device; and a transmitter coupled to the vacuum pressure detector, the transmitter enabled to transmit a wireless signal to a monitor having a receiver for recording a detected vacuum pressure.

* * * * *